United States Patent [19]

Trinh et al.

[11] Patent Number: 5,874,070

[45] Date of Patent: Feb. 23, 1999

[54] COMPOSITIONS FOR REDUCING BODY ODOR

[75] Inventors: Toan Trinh, Maineville; Juliet Marie Lucas, Cincinnati; Robert Gregory Bartolo, Montgomery, all of Ohio; Michael Thomas Dodd, Florence, Ky.; Robin Yager Buckner, Cincinnati; Theresa Marie Kajs, Loveland, both of Ohio

[73] Assignee: The Procter & Gamble Company, Cincinnati, Ohio

[21] Appl. No.: 871,855

[22] Filed: Jun. 9, 1997

[51] Int. Cl.⁶ ............... A61K 7/32; A61K 25/00; A61K 33/10; A61K 33/24

[52] U.S. Cl. ............... 424/65; 422/5; 424/67; 424/69; 424/76.1; 424/76.2; 424/76.21; 424/76.4; 424/76.8; 424/78.03; 424/405; 424/642; 424/715; 424/717

[58] Field of Search ............... 424/65, 67, 69, 424/76.1, 76.2, 76.21, 76.4, 76.8, 78.03, 405, 642, 715, 717; 422/5

[56] References Cited

U.S. PATENT DOCUMENTS

| | | | |
|---|---|---|---|
| 3,574,821 | 4/1971 | Pfirmann et al. | 424/45 |
| 4,278,658 | 7/1981 | Hooper et al. | 424/65 |
| 4,382,079 | 5/1983 | Marschner | 424/65 |
| 4,659,696 | 4/1987 | Hirai et al. | 514/15 |
| 4,788,060 | 11/1988 | Endicott et al. | 424/443 |
| 4,822,602 | 4/1989 | Sabatelli | 424/65 |
| 4,904,524 | 2/1990 | Yoh | 428/311.3 |
| 5,429,628 | 7/1995 | Trinh et al. | 604/359 |
| 5,486,355 | 1/1996 | Berschied, Jr. | 424/65 |
| 5,513,199 | 4/1996 | Khan et al. | 252/106 |
| 5,514,367 | 5/1996 | Lentuni et al. | 424/59 |
| 5,518,727 | 5/1996 | Lajoie et al. | 424/400 |
| 5,540,853 | 7/1996 | Trinh et al. | 510/101 |
| 5,552,378 | 9/1996 | Trinh et al. | 512/3 |
| 5,578,563 | 11/1996 | Trinh et al. | 510/513 |
| 5,580,851 | 12/1996 | Trinh et al. | 512/4 |
| 5,593,670 | 1/1997 | Trinh et al. | 424/76.1 |
| 5,635,165 | 6/1997 | Pantich | 424/65 |

FOREIGN PATENT DOCUMENTS

| | | |
|---|---|---|
| 0 613 675 A1 | 9/1994 | European Pat. Off. |
| 0 701 812 A1 | 3/1996 | European Pat. Off. |
| 2201880 | 5/1974 | France. |
| 87637 | 11/1972 | Germany. |
| 2731520 | 1/1979 | Germany. |
| 208482 B SHO | 8/1992 | Hungary. |
| 53-41440 SHO | 4/1978 | Japan. |
| 58-124452 SHO | 7/1983 | Japan. |
| 61-128973 SHO | 6/1986 | Japan. |
| 63-164953 | 7/1988 | Japan. |
| HEI 3-170415 | 7/1991 | Japan. |
| HEI 3-284616 | 12/1991 | Japan. |
| HEI 5-269185 | 10/1993 | Japan. |

| | | |
|---|---|---|
| WO 95/17175 | 6/1995 | WIPO. |
| WO 96/04940 | 2/1996 | WIPO. |

OTHER PUBLICATIONS

H. Matsuda, et al., "Application of 2–Hydroxypropyl–β–Cyclodextrin to Perfumes and Cosmetics", The 7th International Cyclodextrins Symposium, Tokyo, Japan, Apr. 25–28, 1994, pp. 516–19.

Hashimoto, H., "Studies on the Industrial Production and Application of Cyclodextrins", Starch Science, vol. 36, No. 1 (1989), pp. 35–42.

Hashimoto, H., "Application of Cyclodextrins to Foods, Toiletries and Other Products in Japan", Ensuiko Sugar Refining Co., Ltd., pp. 13–46 No Date.

U.S. application No. 08/736,469, Trinh, et al., filed Oct. 24, 1996.

U.S. application No. 08/736,093, Trinh, et al., filed Oct. 24, 1996.

U.S. application No. 08/889,607, Trinh, et al., filed Jul. 8, 1997.

U.S. application No. 08/736,471, Lucas, et al., filed Oct. 24, 1996.

U.S. application No. 08/736,470, Lucas, et al., filed Oct. 24, 1996.

U.S. application No. 08/738,964, Dodd, et al., filed Oct. 24, 1996.

U.S. application No. 08/736,838, Peterson, et al., filed Oct. 28, 1996.

U.S. application No. 08/739,091, Peterson, et al., filed Oct. 28, 1996.

U.S. application No. 08/871,166, Lucas et al., filed Jun. 9, 1997.

U.S. application No. 08/871,854, Lucas, et al., filed Jun. 9, 1997.

U.S. application No. 08/871,791, Dodd, et al., filed Jun. 9, 1997.

U.S. application No. 08/871,853, Lucas, et al., filed Jun. 9, 1997.

U.S. application No. 08/871,857, Lucas, et al., filed Jun. 9, 1997.

U.S. application No. 08/871,790, Peterson, et al., filed Jun. 9, 1997.

(List continued on next page.)

Primary Examiner—Shelley A. Dodson
Attorney, Agent, or Firm—Kirsten K. Stone; Mary Catherine Hentz; Douglas C. Mohl

[57] ABSTRACT

The present invention relates to a perfumed aqueous, odor absorbing composition comprising from about 0.1% to about 5%, by weight of the composition, of solubilized, water-soluble, uncomplexed cyclodextrin; from about 0.5% to about 30%, by weight of the composition, of a linear dimethicone having a nominal viscosity of 350 centistokes or less; from about 0.004% to about 2%, by weight of the composition, of a perfume composition; and an aqueous carrier; wherein the perfume composition is safe for use on skin. The odor absorbing compositions of the present invention may also contain an effective amount of solubilized, water-soluble, antimicrobial.

14 Claims, No Drawings

OTHER PUBLICATIONS

U.S. application No. 08/871,856, Peterson, et al., filed Jun. 9, 1997.
U.S. application No. 08/871,858, Lucas, et al., filed Jun. 9, 1997.
U.S. application No. 08/871,577, Lucas, et al., filed Jun. 9, 1997.
U.S. application No. 08/871,860, Lucas, et al., Jun. 9, 1997.
U.S. application No. 08/871,861, Peterson, et al., filed Jun. 9, 1997.
U.S. application No. 08/871,092, Peterson, et al., filed Jun. 9, 1997.
U.S. application No. 08/289,732, Trinh, et al., filed Aug. 12, 1994.
U.S. application No. 08/289,733, Trinh, et al., filed Aug. 12, 1994.
U.S. application No. 08/289,734, Cappel, et al., filed Aug. 12, 1994.
U.S. application No. 08/289,735, Cappel, et al., filed Aug. 12, 1994.
U.S. application No. 08/289,969, Pilosof, et al., filed Aug. 12, 1994.
U.S. application No. 08/871,576, Woo, et al., filed Jun. 9, 1997.
U.S. application No. 08/871,119, Woo et al., filed Jun. 9, 1997.
U.S. application No. 08/871,042, Woo et al., filed Jun. 9, 1997.

COMPOSITIONS FOR REDUCING BODY ODOR

BACKGROUND OF THE INVENTION

Body odor is most commonly caused by fatty acids on skin and by malodors from microbial sources. The human skin is naturally populated with numerous micro-organisms which are nourished by various skin secreted substances (eccrine and apocrine sweat, and sebum), skin cell debris, breakdown products of the skin and the organisms themselves. These unpleasant body odors are mainly organic molecules which have different structures and functional groups, such as amines, acids, alcohols, aldehydes, ketones, phenolics, polycyclics, indoles, aromatics, polyaromatics, etc. They can also be made up of sulfur-containing functional groups, such as, thiol, mercaptan, sulfide and/or disulfide groups.

Numerous attempts have been made to control or absorb body odors. Attempts have been made to deprive the microbials responsible for body odor of the moist/humid environment they need to proliferate and grow. Such efforts include the use of powders and/or antiperspirants. Body powders often are undesirable as they may be difficult to apply and may rub or fall off onto clothing. Antiperspirants are not always preferred in a body odor control product since, when used over the entire body, they may interfere with the body's thermal regulatory process by inhibiting perspiration through the action of astringent salts. Additionally, such salts may be irritating to a large number of users, particularly when applying them to sensitive areas such as the pelvic region.

Other deodorant compositions aimed at combating/controlling odor associated with skin secretions, which have been described in the chemical and cosmetic literature, include emulsion sticks or suspensoid sticks, aerosols, roll-ons, pads, pump sprays, and even soap bars. These known deodorants attempt to control odor through a variety of means. For instance, U.S. Pat. No. 5,525,331, to Betts, issued Jun. 11, 1996, discloses compositions which inhibit the growth of micro-organisms in the body-secretions. Deodorants may also include antibacterial compounds which help destroy/control the amount of bacteria present on skin, thereby minimizing odor produced via bacterial metabolism of skin secretions.

Zeolites are known odor absorbers. However, these solid odor absorbers, in addition to known activated charcoal odor absorbers, lose functionality when wet. Therefore, when wetted by body fluids or when carried in an aqueous solution, these odor absorbers are not preferred as they lose their desired odor absorbent characteristics. Furthermore, zeolites can cause "harsh" feel if too much is deposited onto the skin.

In addition to the aforementioned attempts at controlling and/or absorbing body odor, numerous attempts have been made to mask body odors with other odors or perfumes. However, perfumes are often inadequate at fully concealing body odors and may be irritating to the user when used alone for control odor.

Thus, there remains a need for a safe and effective perfumed odor absorbing composition, which is essentially free of astringent antiperspirants and is capable of absorbing a broad spectrum of body odors that are not fully suppressed by the aforementioned means. It has been discovered that such enhanced body odor control can be safely provided to the entire body by application of a composition, which is left on the skin, which incorporates odor absorbing, uncomplexed cyclodextrins into an aqueous solution. Surprisingly, it has been discovered that perfume compositions may be added to the above-mentioned compositions without defeating the body odor absorption utility of the uncomplexed cyclodextrins. Furthermore, it has been discovered that the combination of cyclodextrins with low levels of antimicrobials provides optimal body odor absorbing characteristics. It has also been discovered that a particular advantage of the present invention is the ability to provide convenient, non-irritating odor protection when applied to occluded skin areas such as the pelvic region, the external vagina, the panty-line, the bra-line, and skin-folds, which may be very sensitive.

These and other objects of the present invention will become readily apparent from the detailed description which follows. All percentages, ratios, and parts herein, in the Specification, Examples, and claims are by weight unless otherwise stated. The term "g", as used herein, means gram. The term "ml", as used herein, means milliliter. The term "wt", as used herein, means weight.

SUMMARY OF THE INVENTION

The present invention relates to a perfumed aqueous, odor absorbing composition comprising from about 0.1% to about 5%, by weight of the composition, of solubilized, water-soluble, uncomplexed cyclodextrin; from about 0.5% to about 30%, by weight of the composition, of a linear dimethicone having a nominal viscosity of 350 centistokes or less; from about 0.004% to about 2%, by weight of the composition, of a perfume composition; and an aqueous carrier; wherein the perfume composition is safe for use on skin. The odor absorbing compositions of the present invention may also contain an effective amount of solubilized, water-soluble, antimicrobial.

DETAILED DESCRIPTION OF THE INVENTION

The present invention relates to a perfumed odor-absorbing composition which is useful in reducing body odor and/or vaginal odor on skin. The present invention also relates to the pre-formed wipes comprising odor absorbing compositions deposited on flexible dispensing means. The present invention also relates also relates to use of an article of manufacture comprising the odor-absorbing composition deposited on a flexible dispensing means.

The term "body fluids", as used herein, includes eccrine sweat, apocrine sweat, sebum, build up of sensible moisture from transepidermal water loss, vaginal discharge, urine, and mixtures thereof. The term "body odor" as used herein means odors which are generated as a result of the natural functioning of a human or mammalian body. Such odors include, but are not limited to odors produced by microorganisms of the skin (i.e. bacterial decomposition of skin secretions), urine, or vaginal discharge, and mixtures thereof. The term "skin" means human or mammalian skin. The term "entire body" means the entire external surface of human or mammalian skin. The term "vaginal odor" relates specifically to those body odors which emanate from the pelvic region of a woman, particularly the vagina and the panty line.

A detailed description of the methods, and of the essential and optional components of the odor absorbing compositions useful in the present invention is given below.

CYCLODEXTRIN: As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The term "uncomplexed cyclodextrin" as used herein means that the cavities within the cyclodextrin in the solution of the present invention should remain essentially unfilled while in solution, in order to allow the cyclodextrin to absorb various odor molecules when the solution is applied to a surface. The term "water-soluble, uncomplexed cyclodextrin" as used herein means uncomplexed cyclodextrin having a minimum solubility limit of 1% (1 gram in 100 grams of water).

Preferred, the cyclodextrins used in the present invention are highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Highly water-soluble cyclodextrins are those having water solubility of at least about 10 g in 100 ml of water at room temperature, preferably at least about 20 g in 100 ml of water, more preferably at least about 25 g in 100 ml of water at room temperature. The preferred highly water-soluble cyclodextrins are hydroxypropyl beta-cyclodextrin and methylated beta-cyclodextrin. More preferred are beta cyclodextrin, hydroxypropyl alpha-cyclodextrin, hydroxypropyl beta-cyclodextrin, methylated-alpha-cyclodextrin or methylated-beta-cyclodextrin. Non-derivatised beta-cyclodextrin can be present at a level up to its solubility limit of about 1.85% at room temperature. When beta-cyclodextrin is applied to a wipe substrate, levels higher than its solubility limit can be used.

It is also preferable to use a mixture of cyclodextrins. Such mixtures absorb body odors more broadly by complexing with a wider range of odoriferous molecules having a wider range of molecular sizes. Preferred are mixtures of beta-cyclodextrin and/or its derivatives with alpha-cyclodextrin and/or its derivatives, and mixtures thereof. The levels of cyclodextrin are from about 0.1% to about 5%, preferably from about 0.2% to about 4%, more preferably from about 0.3% to about 3%, most preferably from about 0.4% to about 2%, by weight of the composition.

Concentrated compositions can also be used. When a concentrated product is used, i.e., when the level of cyclodextrin used is from about 3% to about 10%, it is preferable to dilute the composition before applying to the skin in order to avoid tacky skin feel and/or an undesirable amount of residue. Preferably the cyclodextrin is diluted with about 50% to about 2000%, more preferably with about 60% to about 1000%, most preferably with about 75% to about 500%, by weight of the composition, of water.

The complexation between cyclodextrin and odorous molecules occurs rapidly in the presence of water when the solubilized cyclodextrins are first applied to the skin. Additionally, cyclodextrins which dry on the skin surfaces will once again achieve enhanced absorption capabilities when rewetted with body fluids. This is convenient for the user because the cyclodextrins, while on dry skin, will not readily fill their cavities with other environmental odors which would otherwise render them less efficient for absorbing body odors. More particularly, upon solubilization of the cyclodextrins by the body fluids, the isolated cavities become available to form inclusion complexes with the body odor molecules. Thus, ultimately, the availability of solubilized uncomplexed cyclodextrin is essential for an effective and efficient odor control performance. A more complete description of the cyclodextrins and cyclodextrin derivatives useful in the present invention can be found in U.S. Pat. No. 5,534,165, Pilosof et al., issued Jul. 9, 1996, which is incorporated herein by reference in its entirety.

DIMETHICONE: The compositions of the present invention may optionally, but preferably comprise an effective level of dimethicone, which aids in preventing or reducing skin irritation and also may contribute other benefits such as reducing skin-to-skin friction. An "effective level" of dimethicone, as used herein, is a level which effectively provides the desired skin benefits of dimethicone. The dimethicones used in the present invention must be linear dimethicones having nominal viscosities of 350 centistokes or less. Preferred is a linear dimethicones having a nominal viscosities of from about 50 centistokes to about 100 centistokes, available as Dow Corning® 200 Fluid. Typically, the dimethicone is present at a level of from about 0.5% to about 30% preferably from about 1% to about 2%, by weight of the composition.

PERFUME COMPOSITION: The present invention includes a perfume composition at a level which is non-irritating to the ordinary user's skin and/or respiratory tract, yet is discernible by the human sense of smell before and/or after application to the skin. The perfume composition should be one which is safe for use on skin. The phrase "safe for use on skin" as used herein means that the composition provides the desired benefit without undue adverse side effects. The perfume compositions useful herein are comprised of perfume ingredients. The perfume composition is typically present at a level of from about 0.004% to about 2%, preferably from about 0.005% to about 1%, more preferably from about 0.006% to about 0.6%, and most preferably from about 0.007% to about 0.3%, by weight of the odor absorbing composition.

It is essential that the perfume composition be added at a level wherein even if all of the perfume composition were to complex with the cyclodextrin molecules, there will still be an effective level of uncomplexed cyclodextrin molecules present in the odor absorbing composition to provide adequate odor control. In order to reserve an effective amount of cyclodextrin molecules for odor control, the perfume composition is typically present at a level wherein less than about 90%, preferably less than about 50%, more preferably less than about 30%, and most preferably less than about 10% of the cyclodextrin complexes with the perfume composition. The cyclodextrin to perfume composition weight ratio should be greater than about 8:1, preferably greater than about 10:1, more preferably greater than about 20:1, even more preferably greater than 40:1 and most preferably greater than about 70:1.

Any type of perfume ingredient can be incorporated into the perfume composition. However, preferably the perfume composition is composed predominantly of perfume ingredients selected from two groups of perfume ingredients, namely, (I) hydrophilic perfume ingredients having a ClogP of less than about 3.5, more preferably less than about 3.0, and (II) ingredients having significant low odor detection threshold, and mixtures thereof. Typically, the perfume ingredients of the above groups (I) and (II) are present in at least about 50%, preferably at least about 60%, more preferably at least about 70%, and most preferably at least about 80% by weight of the perfume composition.

I. Hydrophilic Perfume Ingredients: The hydrophilic perfume ingredients are more water soluble, have less a tendency to complex with the cyclodextrins, and are more available in the odor absorbing composition. The degree of hydrophobicity of a perfume ingredient can be correlated with its octanol/water partition coefficient P. Since the partition coefficients of the perfume ingredients normally have high values, they are more conveniently given in the form of their logarithm to the base 10, "logP". "CLOGP" values are calculated logP values available from Daylight Chemical Information Systems, Inc., Irvine, Calif. Preferred hydrophilic perfume ingredients of this invention have logP of about 3.5 or smaller, preferably of about 3.0 or smaller. Octanol/water partition coefficients are described in detail in U.S. Pat. No. 5,578,563, to Trinh, issued Nov. 26, 1996, which is incorporated herein by reference in its entirety.

Non-limiting examples of the more preferred perfume ingredients are allyl amyl glycolate, allyl caproate, amyl acetate, amyl propionate, anisic aldehyde, anisyl acetate, anisole, benzaldehyde, benzyl acetate, benzyl acetone, benzyl alcohol, benzyl formate, benzyl iso valerate, benzyl propionate, beta gamma hexenol, calone, camphor gum, laevo-carveol, d-carvone, laevo-carvone, cinnamic alcohol, cinnamyl acetate, cinnamic alcohol, cinnamyl formate, cinnamyl propionate, cis-jasmone, cis-3-hexenyl acetate, cuminic alcohol, cuminic aldehyde, Cyclal C, cyclogalbanate, dihydroeuginol, dihydro isojasmonate, dimethyl benzyl carbinol, dimethyl benzyl carbinyl acetate, ethyl acetate, ethyl aceto acetate, ethyl amyl ketone, ethyl anthranilate, ethyl benzoate, ethyl butyrate, ethyl cinnamate, ethyl hexyl ketone, ethyl maltol, ethyl-2-methyl butyrate, ethyl methylphenyl glycidate, ethyl phenyl acetate, ethyl salicylate, ethyl vanillin, eucalyptol, eugenol, eugenyl acetate, eugenyl formate, eugenyl methyl ether, fenchyl alcohol, flor acetate (tricyclo decenyl acetate), fructone, frutene (tricyclo decenyl propionate), geraniol, geranyl oxyacetaldehyde, heliotropin, hexenol, hexenyl acetate, hexyl acetate, hexyl formate, hinokitiol, hydratropic alcohol, hydroxycitronellal, hydroxycitronellal diethyl acetal, hydroxycitronellol, indole, isoamyl alcohol, iso cyclo citral, isoeugenol, isoeugenyl acetate, isomenthone, isopulegyl acetate, isoquinoline, keone, ligustral, linalool, linalool oxide, linalyl formate, lyral, menthone, methyl acetophenone, methyl amyl ketone, methyl anthranilate, methyl benzoate, methyl benzyl acetate, methyl cinnamate, methyl dihydrojasmonate, methyl eugenol, methyl heptenone, methyl heptine carbonate, methyl heptyl ketone, methyl hexyl ketone, methyl isobutenyl tetrahydropyran, methyl-N-methyl anthranilate, methyl beta naphthyl ketone, methyl phenyl carbinyl acetate, methyl salicylate, nerol, nonalactone, octalactone, octyl alcohol (octanol-2), para-anisic aldehyde, para-cresol, para-cresyl methyl ether, para hydroxy phenyl butanone, para-methoxy acetophenone, para-methyl acetophenone, phenoxy ethanol, phenoxyethyl propionate, phenyl acetaldehyde, phenylacetaldehyde diethyl ether, phenylethyl oxyacetaldehyde, phenyl ethyl acetate, phenyl ethyl alcohol, phenyl ethyl dimethyl carbinol, prenyl acetate, propyl butyrate, pulegone, rose oxide, safrole, terpineol, vanillin, and viridine.

Non limiting examples of other preferred hydrophilic perfume ingredients useful herein are allyl heptoate, amyl benzoate, anethole, benzophenone, carvacrol, citral, citronellol, citronellyl nitrile, cyclohexyl ethyl acetate, cymal, 4-decenal, dihydro isojasmonate, dihydro myrcenol, ethyl methyl phenyl glycidate, fenchyl acetate, florhydral, gamma-nonalactone, geranyl formate, geranyl nitrile, hexenyl isobutyrate, alpha-ionone, isobornyl acetate, isobutyl benzoate, isononyl alcohol, isomenthol, para-isopropyl phenylacetaldehyde, isopulegol, linalyl acetate, 2-methoxy naphthalene, menthyl acetate, methyl chavicol, beta naphthol methyl ether, neral, nonyl aldehyde, phenyl heptanol, phenyl hexanol, terpinyl acetate, Veratrol, and yara—yara.

The preferred perfume compositions contain at least 5, preferably at least 6, more preferably at least 7, and even more preferably at least 8 different hydrophilic perfume ingredients. Most common perfume ingredients which are derived from natural sources are composed of a multitude of components. When each such material is used in the formulation of the preferred perfume compositions herein, it is counted as one single ingredient, for the purpose of defining the invention.

II. Perfume Ingredients having Low Odor Detection Thresholds: The use of small amounts of perfume ingredients that have low odor detection threshold values can improve perfume odor character, even though they are not as hydrophilic as perfume ingredients of group (I) which are given herein above. The phrase "odor detection threshold" of an odorous material means the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990; and "Compilation of Odor and Taste Threshold Values Data", F. A. Fazzalari, editor, ASTM Data Series DS 48A, American Society for Testing and Materials, 1978, both of said publications being incorporated by reference. Perfume ingredients that do not belong to group (I) above, but have a significantly low odor detection threshold, useful herein, are selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof. These materials are preferably present in addition to the hydrophilic ingredients of group (I), typically at less than about 20%, preferably less than about 15%, more preferably less than about 10%, by weight of the perfume compositions.

There are also hydrophilic ingredients of group (I) that have a significantly low odor detection thresholds, and are useful herein. Examples of these ingredients are allyl amyl glycolate, anethole, benzyl acetone, calone, cinnamic alcohol, cyclogalbanate, Cyclal C, cymal, 4-decenal, dihydro isojasmonate, ethyl anthranilate, ethyl-2-methyl butyrate, ethyl methylphenyl glycidate, ethyl vanillin, eugenol, flor acetate, florhydral, fructone, frutene, heliotropin, keone, indole, iso cyclo citral, isoeugenol, lyral, methyl heptine carbonate, linalool, methyl anthranilate, methyl dihydrojasmonate, methyl isobutenyl tetrahydropyran, methyl beta naphthyl ketone, beta naphthol methyl ether, nerol, para-anisic aldehyde, para hydroxy phenyl butanone, phenyl acetaldehyde, vanillin, and mixtures thereof.

AQUEOUS CARRIER: The cyclodextrins useful in the present invention should be solubilized in and dispersed in an aqueous carrier. The aqueous carrier provides a clean, convenient means for applying cyclodextrin to desired skin sites. The aqueous carrier also may impart a degree of cleaning power in and of itself via washing away skin cell debris and skin secretions which bacteria feed upon, as well as the bacteria themselves.

The term "aqueous carrier", as used herein, means water and/or any water soluble materials suitable for use as solvents. Any water may be used, such as distilled, deionized, or tap water. Water not only serves as the liquid carrier for the cyclodextrins, but it also facilitates the complexation reaction between the cyclodextrin molecules and any malodorous molecules that are on the skin site when the composition is applied. The aqueous carrier of the present invention will typically comprise from about 80% to about 98%, preferably from about 85% to about 95% of the present invention's composition.

WATER-SOLUBLE ANTIMICROBIAL: The compositions may optionally but preferably contain solubilized, mild, water-soluble, antimicrobials which are effective for inhibiting and/or regulating microbial growth in the composition and/or on skin. Contamination of the compositions of the present invention by microorganisms and subsequent microbial growth can result in unsightly or malodorous compositions. Similarly, microorganisms are typically found in cyclodextrin supplies and their growth in aqueous solutions is possible. Therefore, the inclusion of antimicrobials as preservatives aids in increasing storage stability of the composition of the present invention. When included for preservative action, the water-soluble antimicrobials are included in an effective amount to prevent spoilage or prevent growth of microorganisms inadvertently added to the composition for a specific period of time. If antimicrobial action on skin is desired, water-soluble antimicrobials must be included at a level effective to perform the preservative action discussed above, and to kill and/or prevent growth of microorganisms on the skin.

Antimicrobials useful herein include biocidal and biostatic compounds (substances that kill microorganisms and/or regulate the growth of microorganisms). Suitable water-soluble antimicrobial preservatives have a solubility of 0.3% or greater. In addition, suitable preservatives are those which can come into contact with skin without high irritation potential. Preferred antimicrobial preservatives are those that are water-soluble and are effective at low levels because the water insoluble organic preservatives can form inclusion complexes with the cyclodextrin molecules and compete with the malodorous molecules for the cyclodextrin cavities, thus rendering the cyclodextrins ineffective as odor controlling actives. Preservatives suitable for use in the present compositions are fully described in *The Theory and Practice of Industrial Pharmacy*, by Lachman, Lieberman, Kanig, 3rd. Edition, pages 466–467 and 520–522 (1986), and U.S. Pat. No. 5,534,165, to Pilosof et al., issued Jul. 9, 1996, both of which are incorporated herein by reference.

It is preferable to use a broad spectrum preservative such as one that is effective both on bacteria (both gram positive and gram negative) and fungi. A limited spectrum preservative such as one that is only effective on a single group of microorganisms, for example fungi, can be used in combination with a broad spectrum preservative or other limited spectrum preservatives with complimentary and/or supplementary activity. A mixture of broad spectrum preservatives can also be used.

Preferred water-soluble preservatives include: sodium hydroxymethylglycinate (i.e. Suttocide® A. from Sutton Labs, Chatham, N.J.), cyclic organic nitrogen compounds including imidazolidinedione compounds (such as dimethyloldimethylhydantoin i.e., Glydant® Plus from Lonza, Fair Lawn, N.J.; diazolidinyl urea and imidazolidinyl urea) and polymethoxy bicyclic oxazolidine; phenyl and phenoxy compounds including benzyl alcohol, 2-phenoxyethanol and hexamidine isethionate; quaternary ammonium compounds including polyhexamethylene biguanide; low molecular weight aldehydes including formaldehyde and glutaraldehyde; halogenated compounds including chlorhexidine, chlorobutanol, and dibromopropamidine; and mixtures thereof.

Preferred levels of antimicrobial are from about 0.0001% to about 0.6%, more preferably from about 0.0002% to about 0.55%, most preferably from about 0.0003% to about 0.5%, by weight of the composition.

pH: Aqueous compositions of the present invention should have a pH of from about 3 to about 10, preferably from about 3.5 to about 8, more preferably from about 3.5 to about 6. Some conventional buffering agents are known in the prior art which may be used to adjust the pH to the desired level if necessary. For example, combinations of salts and acids, such as the following examples: sodium lactate, sodium citrate, potassium phosphate, lactic acid, citric acid, phosphoric acid, hydrochloric acid, and sodium hydroxide are useful. Some of the effectiveness of these ingredients may be lost as they complex with the cyclodextrin, so care is taking in formulating to adjust for that. Other optional buffers appear in *The Theory and Practice of Industrial Pharmacy*, Lachman, Lieberman and Kanig, Third Edition, incorporated herein by reference.

OPTIONAL INGREDIENTS: The present composition may also optionally comprises low molecular weight polyols. The phrase "low molecular weight polyols", as used herein, refers to linear organic compounds with more than one alcohol functional group per molecule wherein the molecular weight is less than 95. Low molecular weight polyols with relatively high boiling points, as compared to water, such as propylene glycol and glycerol are preferred ingredients which may improve odor control performance of the composition of the present invention. Cyclodextrins prepared by processes that result in a level of such polyols are highly desirable, since they can be used without removal of the polyols.

Optimally, the low molecular weight polyols will be added at a level effective to assist in complex formation without significantly reducing available cyclodextrin capacity to absorb the malodor molecules having larger sizes. Typically, low molecular weight polyols are added to the composition of the present invention at a level of from about 0.01% to about 1%, by weight of the composition, preferably from about 0.02% to about 0.5%, more preferably from about 0.03% to about 0.3%, by weight of the composition.

The composition of the present invention can also, optionally, contain adjunct odor-controlling materials, such as zinc salts, water-soluble cationic polymers, water-soluble anionic polymers, water-soluble carbonate salts, water-soluble bicarbonate salts, zeolites, and activated carbon; chelating agents; colorants; and/or antiperspirants.

Optionally, but highly preferred, the present invention can include zinc salts for added odor absorption and/or antimicrobial benefit for the cyclodextrin solution. Zinc compounds have been used to ameliorate malodor, e.g., in mouth wash products, as disclosed in U.S. Pat. Nos. 4,325,939, issued Apr. 20, 1982 and 4,469,674, issued Sep. 4, 1983, to N. B. Shah, et al., both of which are incorporated herein by reference in their entireties. Highly-ionized and water soluble zinc salts, such as zinc chloride, provide the best source of zinc ions. Zinc phenolsulfonate is preferred for use in the skin composition of the present invention; although others may also fall within the scope of the present invention. However, care must be taken in selecting zinc salts as well as their levels, since some may be irritants to the skin and therefore are not preferred for use in the present invention.

These zinc salts aid in absorbing low molecular weight amine and sulfur-containing compounds. Low molecular weight amines and/or low molecular weight sulfur-containing materials such as sulfide and mercaptans; are components of many types of malodors such as food odors (garlic, onion), breath odor, urine odors, and particularly body/perspiration odor. When zinc salts are added to the composition of the present invention they are typically present at a level of from about 0.1% to about 10%, preferably from about 0.2% to about 8%, more preferably from about 0.3% to about 5%, by weight of the composition.

Some water-soluble polymers such as water-soluble cationic polymer and water-soluble anionic polymers can be used in the composition of the present invention to provide additional odor control benefits. Water-soluble cationic polymers such as those containing amino functionalities, amido functionalities, and mixtures thereof, are useful in the present invention to control certain acid-type odors. Water-soluble anionic polymers such as polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990, to N. Kobayashi and A. Kawazoe, incorporated herein by reference, in its entirety. Another example of water-soluble polymers containing both cationic and anionic functionalities is a copolymer of dimethyldiallyl ammonium chloride and acrylic acid, commercially available under the trade name Merquat 280® from Calgon. While the aforementioned water soluble polymers are useful in the present invention, when using these materials, care must be taken to insure no residual acrylic acid is present due to safety concerns associated with the presence of acrylic acid.

Water-soluble alkali metal carbonate and/or bicarbonate salts, such as sodium bicarbonate, potassium bicarbonate, potassium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. It is also preferred that incompatible metal salts not be present in the invention. Therefore, when these salts are used, the composition should be essentially free of zinc and other incompatible metal ions, e.g., Ca, Fe, etc. which form water-insoluble salts.

Aminocarboxylic acid chelating agents such as ethylenediaminetetraacetic acid (EDTA) can optionally be added to the composition of the present invention (preferably in the absence of any added metal ions) in order to enhance the activity of the water-soluble, antimicrobial preservative. When a chelating agent is added to the composition of the present invention, it is typically present at a level of from about 0.01% to about 0.3%, preferably from about 0.01% to about 0.2% by weight of the composition.

Zeolites can also be used in the present invention. A preferred class of zeolites are characterized as "intermediate" silicate/aluminate zeolites, particularly for use in absorbing amine-type odors. "High" zeolites are preferred for control of sulfur-containing odors, e.g., thiols, mercaptans. Zeolites, both "intermediate" and "high", are explained more fully in U.S. Pat. No. 5,429,628, to Trinh et al., issued Jul. 4, 1995, which is incorporated herein by reference in its entirety.

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such tradenames as; Calgon-Type CPG®; Type PCB®; Type SGL®; Type CAL®; and Type OL®.

Colorants and dyes can be optionally added to the odor absorbing compositions for visual appeal and performance impression. When colorants are used, care must be taken in the selection of choosing dyes that will not color skin at the levels used. Preferred colorants for use in the present compositions are highly water-soluble dyes, e.g., acid blue 3, acid blue 104, acid green 1, acid green 25, acid yellow 3, acid yellow 73 sodium salt, D&C green no. 5, 6 & 8, D&C yellow no. 7, 8, 10 & 11, D&C violet no. 2, FD&C blue No. 1 & 2, FD&C green no.3, FD&C yellow no. 5 & 6, and mixtures thereof.

Optionally, the present skin composition may also comprise known antiperspirants and/or other known deodorant compositions not explicitly disclosed previously. Examples of antiperspirants appropriate for aqueous solutions include aluminum-zirconium tetrachlorohydrex glycine, aluminum-zirconium pentachlorohydrate, aluminum sesquichlorohydrate, or aluminum chlorhydrate and mixtures thereof.

PROCESS OF MAKING COMPOSITIONS

The present invention is prepared by a process comprising the steps of making a mixture of aqueous carrier and all ingredients (except dimethicone) by mixing until all are dissolved and the mixture is homogenous. The term "homogenous", as used herein, means a uniformly dispersed solution. If dimethicone is used, the process of preparing the composition further comprises mixing the mixture with the dimethicone using high shear (for example using a mill) until the composition is homogenous.

Since the compositions herein are applied directly to skin, various applicators are useful for delivering the compositions to the entire body for maximum odor control. For example, the compositions are preferably deposited on a paper product such as a wipe which later is contacted with the skin to transfer the composition to the skin.

Any wipe structures and/or methods of making the wipe structures commonly known in the art may be used. The wipe comprises a flexible dispensing means. The term "flexible dispensing means", as used herein, includes papers, cloths, non-wovens, films, foams, sponges, rollers, pads, tissues, cotton balls, and the like. Preferred wipe substrates comprise a porous material, such as the non-woven substrates, foams, or sponges, which are capable of holding the composition within the pores of the substrates. Examples of cellulosic non-wovens particularly useful and economic are described in U.S. Pat. No. 4,191,609, Trokhan, issued Mar. 4, 1980. Further description of useful wipes and methods of making said wipes are found in World Patent 95/17175, to Mitra et. al, publication date of Jun. 29, 1995. Both references are incorporated herein by reference in their entireties.

Techniques for combining the wipe substrates with the compositions herein are well known in the art. Examples of common techniques include coating, immersing, dipping, or spraying the wipe substrates with the compositions herein. The compositions herein are added to the wipe substrate at level sufficient to provide the desired odor control and/or other desired skin benefits. A convenient method of combining the composition with the chosen substrate is to place the substrate inside an open package which will ultimately house the finished product until use. The composition is poured onto the substrate and allowed to distribute throughout. It is preferred that the homogenous composition is poured onto each wipe individually rather than onto a stack of wipes. The package is then closed and the wipes ready for use. Packages suitable for use herein are any commonly known in the art and include resealable packages and those suitable for one-time use.

The compositions can also be delivered as a liquids via a spray dispenser or a bottle. Preferred is a manually activated spray dispenser to avoid the use of aerosols which may be irritating to sensitive areas of the body. Spray dispensers are described more fully in U.S. Pat. No. 5,534,165 which is incorporated herein by reference in its entirety.

The following non-limiting examples illustrate the perfume compositions and odor absorbing compositions useful in the present invention.

| PERFUME COMPOSITION A | |
|---|---|
| Perfume Ingredients | Wt. % |
| Benzophenone | 0.50 |
| Benzyl acetate | 3.00 |
| Benzyl propionate | 1.00 |
| beta gamma Hexenol | 0.20 |
| Cetalox | 0.10 |
| cis 3 Hexenyl acetate | 0.15 |
| cis Jasmone | 0.10 |
| cis-3-Hexenyl salicylate | 1.00 |
| Citral | 0.50 |
| Citronellal nitrile | 0.70 |
| Citronellol | 3.65 |
| Cyclal C | 0.30 |
| Cyclo galbanate | 0.40 |
| beta Damascone | 0.05 |
| Dihydro myrcenol | 1.00 |
| Ebanol | 0.50 |
| Flor acetate | 5.00 |
| Florhydral | 0.70 |
| Fructone | 8.50 |
| Frutene | 3.00 |
| Geranyl nitrile | 0.40 |
| Heliotropin | 0.70 |
| Hydroxycitronellal | 2.50 |
| Linalool | 2.00 |
| Linalyl acetate | 1.50 |
| Methyl dihydro jasmonate | 5.00 |
| Methyl heptine carbonate | 0.05 |
| Methyl iso butenyl tetrahydro pyran | 0.15 |
| Methyl phenyl carbinyl acetate | 0.50 |
| Nonalactone | 1.50 |
| P.T. Bucinal | 8.40 |
| para Hydroxy phenyl butanone | 1.30 |
| Phenoxy ethanol | 28.55 |
| Phenyl ethyl acetate | 0.80 |
| Phenyl ethyl alcohol | 10.70 |
| Prenyl acetate | 1.50 |
| Terpineol | 1.50 |
| Verdox | 2.10 |
| Vanillin | 0.50 |

| PERFUME COMPOSITION B | |
|---|---|
| Perfume Ingredients | Wt. % |
| Anisic aldehyde | 2.80 |
| Benzyl acetone | 1.00 |
| cis 3 Hexenyl acetate | 0.30 |
| Citronellal nitrile | 1.30 |
| Citronellol | 6.90 |
| Cyclal C | 0.30 |

-continued

| | |
|---|---|
| Cyclo galbanate | 0.70 |
| Cymal | 1.05 |
| delta Damascone | 0.05 |
| Dihydro myrcenol | 1.30 |
| Dipropylene glycol | 10.20 |
| Dodecalactone | 0.50 |
| Ebanol | 0.10 |
| Ethyl vanillin | 0.10 |
| Flor acetate | 8.00 |
| Florhydral | 1.30 |
| Fructone | 6.00 |
| gamma Methyl ionone | 1.00 |
| Geranyl nitrile | 0.30 |
| Helional | 1.50 |
| Hydroxycitronellal | 2.00 |
| Iso bornyl acetate | 1.80 |
| Ligustral | 0.10 |
| Linalool | 2.50 |
| Methyl dihydro jasmonate | 6.20 |
| Methyl heptine carbonate | 0.10 |
| Methyl iso butenyl tetrahydro pyran | 0.30 |
| Methyl phenyl carbinyl acetate | 1.00 |
| Orange terpenes | 2.00 |
| P.T. Bucinal | 10.00 |
| Phenyl ethyl alcohol | 25.30 |
| Prenyl acetate | 1.50 |
| Verdox | 2.50 |

EXAMPLES I, II, and III

| Ingredients | Example I Wt. % | Example II Wt. % | Example III Wt. % |
|---|---|---|---|
| Tetrasodium EDTA | .10 | 0.10 | |
| Zinc chloride | 1.00 | | 1.00 |
| Suttocide ® A | 0.25 | | 0.50 |
| Glydant ® Plus | 0.20 | 0.30 | |
| Hydroxypropyl beta-cyclodextrin | 5.00 | 1.00 | 3.00 |
| Perfume Composition* | 0.05 | 0.007 | 0.02 |
| Dimethicone (100 centistoke) | 3.00 | 1.00 | |
| Propylene glycol | 0.30 | 0.06 | |
| Distilled Water | Balance | Balance | Balance |

*The perfume composition in Examples I–III may be either of the perfume compositions A or B.

Prepare Examples I and II as follows: Add tetra sodium EDTA to approximately 66% of the distilled water for that formula and mix until dissolved. Then add each of the remaining ingredients, except for the dimethicone, in the order listed above, with mixing. Ensure that each ingredient is either dissolved or the solution is homogenous before adding the next ingredient. Add the remaining water of each of the total formulas and stir until homogenous. Finally, add the dimethicone using high shear until the dimethicone is uniformly dispersed in the water.

Prepare Example III as follows: Add each of the ingredients in the order listed above to about half of the water, with mixing. Ensure that each ingredient is either dissolved or the solution is homogenous before adding the next ingredient. Finally, add the remaining water of each of the total formula and stir until homogenous.

Preparation for Application to Skin: Alternatively, the above Examples I–III may be loaded onto a wipe or poured into a spray device or poured directly onto the skin or flexible dispensing means of the user's choosing for convenient application to the skin. To prepare wipes, place dry fabric or wipe substance inside an open package which will ultimately contain the finished product. Pour the composition onto the fabric to distribute throughout. Close the package for storage until consumer use. To prepare spray, pour the composition into the selected spray package. Close the package for storage until consumer use.

What is claimed:

1. An aqueous odor absorbing composition comprising:
    a. from about 0.1% to about 5%, by weight of the composition, of solubilized, water-soluble, uncomplexed cyclodextrin;
    b. from about 0.5% to about 30%, by weight of the composition, of a linear dimethicone having a nominal viscosity of 350 centistokes or less;
    c. from about 0.004% to about 2%, by weight of the composition, of a perfume composition; and
    d. an aqueous carrier;
   wherein at least about 50% of the perfume composition comprises perfume ingredients selected from the group consisting of hydrophilic perfume ingredients having a ClogP of less than about 3.5, perfume ingredients having significant low odor detection threshold, and mixtures thereof; and wherein the perfume composition is safe for use on skin.

2. The composition of claim 1 wherein the cyclodextrin is selected from the group consisting of beta-cyclodextrin, derivatives of beta-cyclodextrin, alpha-cyclodextrin, derivatives of alpha-cyclodextrin, gamma-cyclodextrin, derivatives of gamma-cyclodextrin, and mixtures thereof.

3. The composition of claim 1 wherein the cyclodextrin is selected from the group consisting of methylated cyclodextrin, hydroxypropyl beta-cyclodextrin, and mixtures thereof.

4. The composition of claim 1 further comprising one or more adjunct odor controlling materials selected from the group consisting of zinc salts, zeolites, activated carbon, water-soluble carbonates, water-soluble bicarbonates, and mixtures thereof.

5. The composition of claim 1 further comprising low molecular weight polyols.

6. A composition composition comprising the composition of claim 1 deposited on a wipe which comprises a flexible dispensing means.

7. An aqueous odor absorbing composition comprising:
    a. from about 0.1% to about 5%, by weight of the composition, of solubilized, water-soluble, uncomplexed cyclodextrin;
    b. from about 0.5% to about 30%, by weight of the composition, of a linear dimethicone having a nominal viscosity of 350 centistokes or less;
    c. an effective amount of solubilized, water-soluble, antimicrobial preservative;
    d. from about 0.004% to about 2%, by weight of the composition, of a perfume composition; and
    e. an aqueous carrier;
   wherein at least about 50% of the perfume composition comprises perfume ingredients selected from the group consisting of hydrophilic perfume ingredients having a ClogP of less than about 3.5, ingredients having significant low odor detection threshold, and mixtures thereof; and wherein the perfume composition is safe for use on skin.

8. The composition of claim 7 wherein the cyclodextrin is selected from the group consisting of beta-cyclodextrins, derivatives of beta-cyclodextrins, alpha-cyclodextrins, derivatives of alpha-cyclodextrins, gamma-cyclodextrins, derivatives of gamma-cyclodextrins, and mixtures thereof.

9. The composition of claim 7 further comprising one or more adjunct odor controlling materials selected from the group consisting of zinc salts, zeolites, activated carbon, water-soluble carbonates, water-soluble bicarbonates, and mixtures thereof.

10. The composition of claim 7 further comprising low molecular weight polyols.

11. The composition of claim 7 wherein the cyclodextrin is selected from the group consisting of methylated cyclodextrin, hydroxypropyl beta-cyclodextrin, and mixtures thereof.

12. A composition composition comprising the composition of claim 7 delivered on a wipe which comprises a flexible dispensing means.

13. A process for making an aqueous odor absorbing composition comprising the steps of:
    a. making a mixture of aqueous carrier, perfume composition, and cyclodextrin, by adding the cyclodextrin and the perfume composition to the aqueous carrier and mixing until the cyclodextrin is dissolved and the mixture is homogenous;
    b. adding dimethicone to the mixture and mixing with high shear until the dimethicone is uniformly dispersed in the mixture.

14. The process according to claim 13 which comprises adding a water soluble antimicrobial preservative to the mixture in step 13(a) and mixing until the water soluble antimicrobial preservative is dissolved and the mixture is homogenous.

* * * * *